(12) United States Patent
Jakobsen et al.

(10) Patent No.: US 7,666,604 B2
(45) Date of Patent: *Feb. 23, 2010

(54) MODIFIED SOLUBLE T CELL RECEPTOR

(75) Inventors: Bent Karsten Jakobsen, Abingdon (GB); Meir Glick, Staughton, MA (US)

(73) Assignee: Immunocore Limited, Oxon (GB)

( * ) Notice: Subject to any disclaimer, the term of this patent is extended or adjusted under 35 U.S.C. 154(b) by 461 days.

This patent is subject to a terminal disclaimer.

(21) Appl. No.: 10/544,448

(22) PCT Filed: Jul. 9, 2003

(86) PCT No.: PCT/GB03/02986

§ 371 (c)(1),
(2), (4) Date: Apr. 5, 2006

(87) PCT Pub. No.: WO2004/074322

PCT Pub. Date: Sep. 2, 2004

(65) Prior Publication Data

US 2007/0082362 A1 Apr. 12, 2007

(30) Foreign Application Priority Data

Feb. 22, 2003 (GB) ................... 0304068.0

(51) Int. Cl.
*G01N 33/53* (2006.01)
(52) U.S. Cl. .................. 435/7.1; 530/350; 530/402
(58) Field of Classification Search ............. 435/7.1; 530/350, 402
See application file for complete search history.

(56) References Cited

U.S. PATENT DOCUMENTS

| | | | |
|---|---|---|---|
| 6,080,840 A | 6/2000 | Bothwell et al. | |
| 6,147,203 A | 11/2000 | Pastan et al. | |
| 7,329,731 B2 * | 2/2008 | Jakobsen et al. | 530/350 |
| 2005/0009025 A1 | 1/2005 | Jakobsen et al. | |

FOREIGN PATENT DOCUMENTS

| | | | |
|---|---|---|---|
| WO | WO 96 21028 A | | 7/1996 |
| WO | WO 99/60120 | * | 11/1999 |
| WO | WO 03 020763 A | | 3/2003 |

OTHER PUBLICATIONS

Weber, S et al, 1992, Nature, 356 (6372): 793-6.*
Chang et al, PNAS, USA, 1994, 91: 11408-11412.*
Muller et al, 1998, FEBS letter, 422(2): 259-264.*
Hastrup et al, 1989, J Clin Pathol, 42 (4): 398-402.*
Bauer et al, 1997, Eur J Immunol, 27: 1366-1373.*
White et al, 2001 (Ann Rev Med, 52: 125-145).*
Boon, 1992 (Adv Can Res, 58:177-210).*
Smith RT, 1994 (Clin Immunol, 41(4): 841-849).*
Bodey et al, 2000, Anticancer Res, 20: 2665-2676.*
Pecorari et al.: "Folding, heterodimeric association and specific peptide recognition of a murine alphabeta T-cell receptor expressed in *Escherichia coli*"; Journal of Molecular Biology; vol. 285, No. 4; Jan. 29, 1999; pp. 1831-1843; XP004457383.
Reiter et al.: "Construction of a Functional Disulfide-Stabilized TCR FV Indicates that Antibody and TCR FV Frameworks are Very Similar in Structure"; Immunity; vol. 2, No. 3; Mar. 1995; pp. 281-287; XP009004075.
Fremont et al:. "Biophysical studies of T-cell receptors and their ligands"; Current Opinion in Immunology; vol. 8, No. 1; Feb. 1996; pp. 93-100; XP002123165.
Golden et al: "High-level production of a secreted, heterodimeric alphabeta murine T-cell receptor in *Escherichia coli*"; Journal of Immunological Methods; vol. 206, No. 1-2; Aug. 7, 1997; pp. 163-169; XP004093129.
Davodeau et al.: "Secretion of Disulfide-Linked Human T-Cell Receptor Gammadelta Heterodimers"; Journal of Biological Chemistry; vol. 268, No. 21; Jul. 25, 1993; pp. 15455-15460; XP002008366.
Paliwal et al.: "Recombinant soluble alphabeta T cell receptors protect T cells from immune suppression: requirement for aggregated multimeric, disulfide-linked alphabeta heterodimers"; Journal of Immunology; vol. 159, No. 4; Aug. 15, 1997; pp. 1718-1727; XP002093583.
Garboczi et al.: "Assembly, specific binding, and crystallization of a human TCR-alphabeta with an antigenic Tax peptide from human T lymphotropic virus type 1 and the Class I MHC molecule HLA-A2"; Journal of Immunology; vol. 157; 1996; pp. 5403-5410; XP002123312.
Garboczi et al.: "Structure of the Complex Between Human T-Cell Receptor, Viral Peptide and HLA-A2"; Nature; vol. 384, No. 6605; Nov. 14, 1996; pp. 134-141; XP001097273.
Karadimitris et al., "Human CD1d-glycolipid tetramers generated by in vitro oxidative refolding chromatography," *Proc. Natl. Acad. Sci. USA* 98, 3294-98, 2001.

* cited by examiner

*Primary Examiner*—Larry R. Helms
*Assistant Examiner*—Minh-Tam Davis
(74) *Attorney, Agent, or Firm*—Banner & Witcoff, Ltd.

(57) ABSTRACT

The present invention provides a soluble T cell receptor (sTCR), which comprises (i) all or part of a TCR $g(a)$ chain, except the transmembrane domain thereof, and (ii) all or part of a TCR $g(b)$ chain, except the transmembrane domain thereof. (i) and (ii) each comprise a functional variable domain and at least a part of the constant domain of the TCR chain, and are linked by a disulphide bond between constant domain residues which is not present in native TCR, characterized in that the sTCR recognizes a CD1-antigen complex, a bacterial superantigen or a peptide-MHC/superantigen complex.

19 Claims, 4 Drawing Sheets

Figure 2a

Atgaaccaagtggagcagagtcctcagtccctgatcatcctggagggaaagaactgcactcttcaatgcaattatacagtga
gccccttcagcaacttaaggtggtataagcaagatactgggagaggtcctgtttccctgacaatcatgactttcagtgagaac
acaaagtcgaacggaagatatacagcaactctggatgcagacacaaagcaaagctctctgcacatcacagcctcccagctc
agcgattcagcctcctacatctgtgtggtgagcgacagaggctcaaccctggggaggctatactttggaagaggaactcagt
tgactgtctggcctgatatccagaacccggatcctgccgtgtaccagctgagagactctaaatccagtgacaagtctgtctgc
ctattcaccgattttgattctcaaacaaatgtgtcacaaagtaaggattctgatgtgtatatcacagacaaatgtgtgctagacat
gaggtctatggacttcaagagcaacagtgctgtggcctggagcaacaaatctgactttgcatgtgcaaacgccttcaacaac
agcattattccagaagacaccttcttccccagcccagaaagttcctaa (SEQ ID 25)

Figure 2b

Atggacatctaccagaccccaagatacctttgttatagggacaggaaagaagatcactctggaatgttctcaaaccatgggc
catgacaaaatgtactggtatcaacaagatccaggaatggaactacacctcatccactattcctatggagttaattccacagag
aagggagatctttcctctgagtcaacagtctccagaataaggacggagcattttcccctgaccctggagtctgccaggccctc
acatacctctcagtacctctgtgccagcagtgaaaacatagggacagcctacgagcagtacttcgggccgggcaccaggct
cacggtcacagaggacctgaaaaacgtgttcccacccgaggtcgctgtgtttgagccatcagaagcagagatctcccacac
ccaaaaggccacactggtgtgcctggccacaggcttctaccccgaccacgtggagctgagctggtgggtgaatgggaag
gaggtgcacagtggggtctgcacagacccgcagcccctcaaggagcagcccgccctcaatgactccagatacgctctga
gcagccgcctgagggtctcggccaccttctggcaggaccccgcaaccacttccgctgtcaagtccagttctacgggctct
cggagaatgacgagtggacccaggatagggccaaacccgtcacccagatcgtcagcgccgaggcctgggggtagagca
gactaa (SEQ ID 26)

Figure 3a mnqveqspqsliilegknctlqcnytvspfsnlrwykqdtgrgpvsltimtfsentksngrytatldadtkqsslhitasql
sdsasyicvvsdrgstlgrlyfgrgtqltvwpdiqnpdpavyqlrdskssdksvclftdfdsqtnvsqskdsdvyitdkcv
ldmrsmdfksnsavawsnksdfacanafnnsiipedtffpspess* (SEQ ID 27)

Figure 3b mdiyqtprylvigtgkkitlecsqtmghdkmywyqqdpgmelhlihysygvnstekgdlssestvsrirtehfpltles
arpshtsqylcassenigtayeqyfgpgtrltvtedlknvfppevavfepseaeishtqkatlvclatgfypdhvelswwv
ngkevhsgvctdpqplkeqpalndsryalssrlrvsatfwqdpmhfrcqvqfyglsendewtqdrakpvtqivsaea
wgrad* (SEQ ID 28)

MODIFIED SOLUBLE T CELL RECEPTOR

This application is a U.S. National Stage application of co-pending PCT application PCT/GB2003/002986 filed Jul. 9, 2003, which was published in English under PCT Article 21(2) on Sep. 2, 2004 and which claims the priority of Great Britain Patent Application No. 0304068.0, filed Feb. 22, 2003. These applications are incorporated herein by reference in their entireties.

The present invention relates to soluble T cell receptors (TCRs) which recognise CD1-antigen complexes, bacterial superantigens and peptide-MHC/superantigen complexes.

BACKGROUND TO THE INVENTION

Native TCRs

As is described in, for example, WO 99/60120 TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MEC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the APC cell surface.

Two further classes of proteins are known to be capable of functioning as TCR ligands. (1) CD1 antigens are MHC class I-related molecules whose genes are located on a different chromosome from the classical MHC class I and class II antigens. CD1 molecules are capable of presenting peptide and non-peptide (eg lipid, glycolipid) moieties to T cells in a manner analogous to conventional class I and class II-MHC-pep complexes. See, for example (Barclay et al, (1997) The Leucocyte Antigen Factsbook 2$^{nd}$ Edition, Acadmeic Press) and (Bauer (1997) Eur J Immunol 27 (6) 1366-1373)) (2) Bacterial superantigens are soluble toxins which are capable of binding both class II MHC molecules and a subset of TCRs. (Fraser (1989) Nature 339 221-223) Many superantigens exhibit specificity for one or two V beta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric αβTCR consists of two polypeptides each of which has a membrane-proximal constant domain, and a membrane-distal variable domain (see FIG. 1). Each of the constant and variable domains includes an intra-chain disulfide bond. The variable domains contain the highly polymorphic loops analogous to the complementarity determining regions (CDRs) of antibodies. CDR3 of the TCR interacts with the peptide presented by MHC, and CDRs 1 and 2 interact with the peptide and the MHC. The diversity of TCR sequences is generated via somatic rearrangement of linked variable (V), diversity (D), joining (J), and constant genes. Functional α chain polypeptides are formed by rearranged V-J-C regions, whereas β chains consist of V-D-J-C regions. The extracellular constant domain has a membrane proximal region and an immunoglobulin region. There is a single α chain constant domain, known as TRAC, and two different β constant domains, known as TRBC1 and TRBC2 (IMGT nomenclature). There are four amino acid changes between these β constant domains, three of which are within the domains used to produce the single-chain TCRs of the present invention. These changes are all within exon 1 of TRBC1 and TRBC2: $N_4K_5$->$K_4N_5$ and $F_{37}$->$Y$ (IMGT numbering, differences TRBC1->TRBC2), the final amino acid change between the two TCR β chain constant regions being in exon 3 of TRBC1 and TRBC2: $V_1$->$E$. The extent of each of the TCR extracellular domains is somewhat variable. However, a person skilled in the art can readily determine the position of the domain boundaries using a reference such as The T Cell Receptor Facts Book, Lefranc & Lefranc, Publ. Academic Press 2001.

Soluble TCRs

Soluble TCRs are useful, not only for the purpose of investigating specific TCR-pMHC interactions, but also potentially as a diagnostic tool to detect infection, or to detect autoimmune disease markers. Soluble TCRs also have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an auto-immune peptide antigen.

Proteins which are made up of more than one polypeptide subunit and which have a transmembrane domain can be difficult to produce in soluble form because, in many cases, the protein is stabilised by its transmembrane region. This is the case for the TCR, and is reflected in the scientific literature which describes truncated forms of TCR, containing either only extracellular domains or extracellular and cytoplasmic domains, which can be recognised by TCR-specific antibodies (indicating that the part of the recombinant TCR recognised by the antibody has correctly folded), but which cannot be produced at a good yield, which are not stable at low concentrations and/or which cannot recognise MHC-peptide complexes. This literature is reviewed in WO 99/60120.

A number of papers describe the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268 (21): 15455-15460; Golden et al., (1997), J. Imm. Meth. 206: 163-169; U.S. Pat. No. 6,080,840). However, although such TCRs can be recognised by TCR-specific antibodies, none were shown to recognise its native ligand at anything other than relatively high concentrations and/or were not stable.

In WO 99/60120, a soluble TCR is described which is correctly folded so that it is capable of recognising its native ligand, is stable over a period of time, and can be produced in reasonable quantities. This TCR comprises a TCR α or γ chain extracellular domain dimerised to a TCR β or δ chain extracellular domain respectively, by means of a pair of C-terminal dimerisation peptides, such as leucine zippers. This strategy of producing TCRs is generally applicable to all TCRs.

Reiter et al, *Immunity*, 1995, 2:281-287, details the construction of a soluble molecule comprising disulphide-stabilised TCR α and β variable domains, one of which is linked to a truncated form of *Pseudomonas* exotoxin (PE38). One of the stated reasons for producing this molecule was to overcome the inherent instability of single-chain TCRs. The position of the novel disulphide bond in the TCR variable domains was identified via homology with the variable domains of antibodies, into which these have previously been introduced (for example see Brinkmann, et al. (1993), *Proc. Natl. Acad. Sci. USA* 90: 7538-7542, and Reiter, et al. (1994) *Biochemistry* 33: 5451-5459). However, as there is no such homology between antibody and TCR constant domains, such a technique could not be employed to identify appropriate sites for new inter-chain disulphide bonds between TCR constant domains.

Given the importance of soluble TCRs, it would be desirable to provide an alternative way of producing such molecules. Specifically it would be desirable to provide alternative soluble TCRs which recognise CD1-antigen complexes, bacterial superantigens and peptide-MHC/superantigen complexes. The TCRs of the present invention provide stable, soluble, polypeptides that can be produced in a wide variety of prokaryotic and eukaryotic expression systems. Bacterial expression is particularly preferred for economic reasons.

BRIEF DESCRIPTION OF THE DRAWINGS

FIGS. 2A and 2B show respectively the nucleic acid sequences of the α and β chains of a soluble CD 1-binding TCR, mutated so as to introduce a cysteine codon. The shading indicates the introduced cysteine codon.

FIG. 3A shows the CD 1-binding TCR α chain extracellular amino acid sequence, including the $T_{48}$->C mutation (underlined) used to produce the novel disulphide inter-chain bond. FIG. 3B shows the CD-1 binding TCR β chain extracellular amino acid sequence, including the $S_{57}$->C mutation (underlined) used to produce the novel disulphide inter-chain bond.

DETAILED DESCRIPTION

Figure 1:
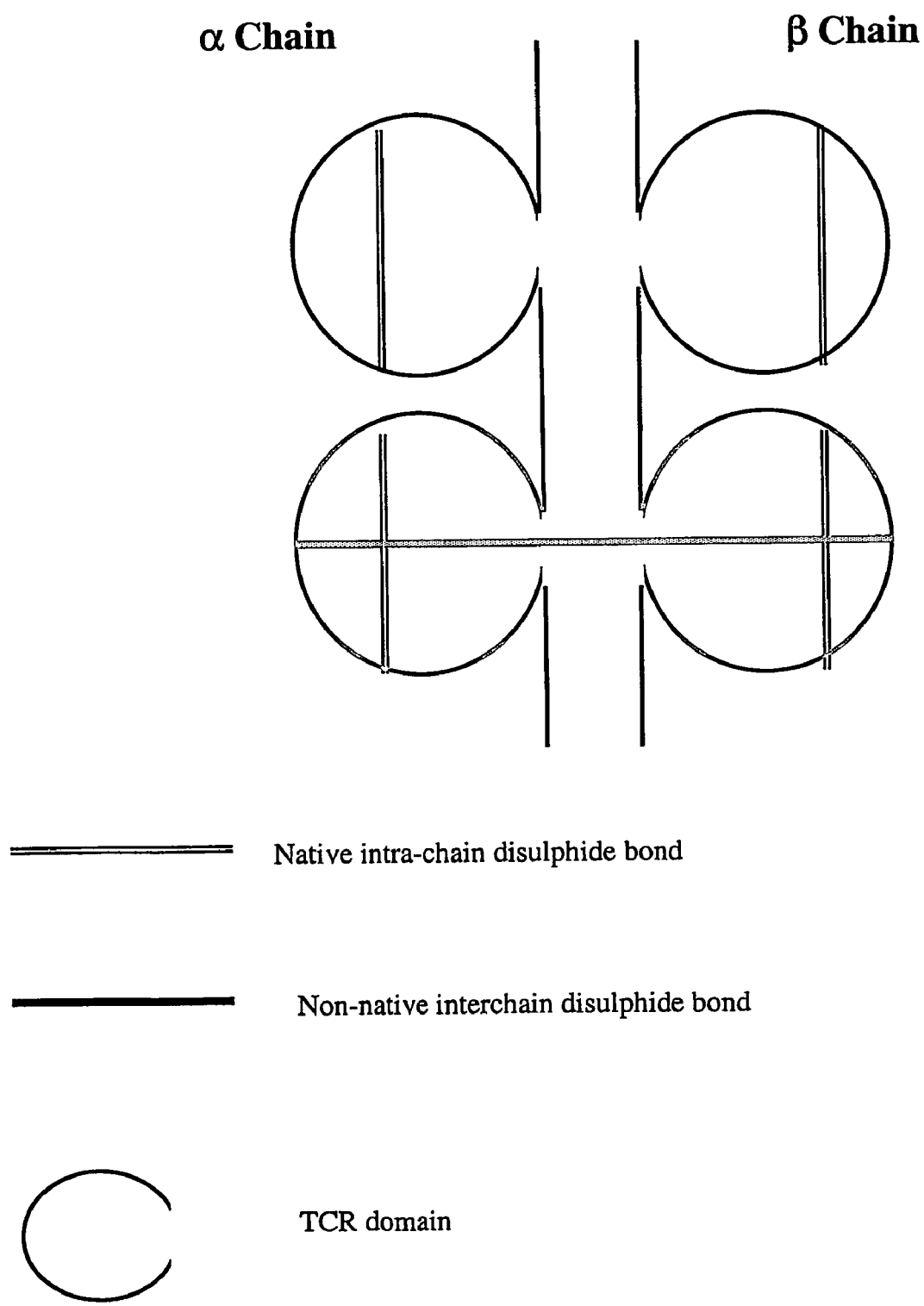
FIG. 1 is a schematic diagram of a soluble TCR with an introduced inter-chain disulphide bond in accordance with the invention.
Figure 4:
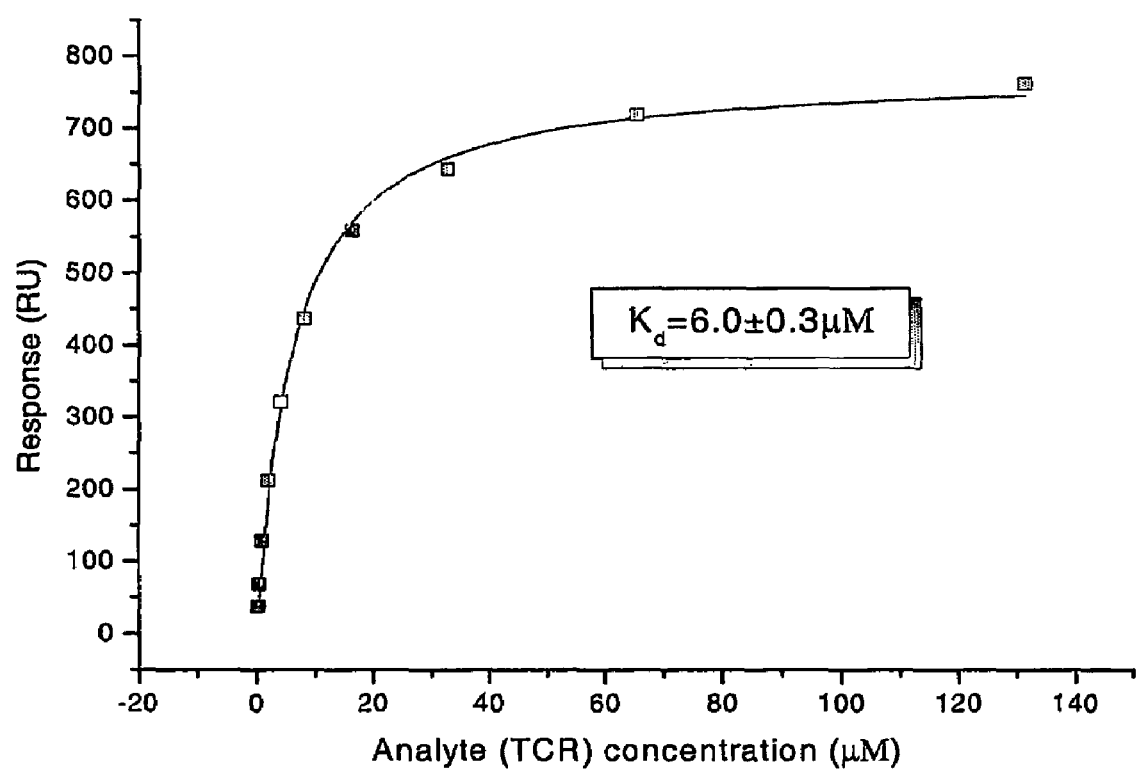
FIG. 4 is a BIAcore response curve of the specific binding of disulphide-linked CD1d-binding soluble TCR to soluble CD1d.

According to a first aspect, the present invention provides a soluble T cell receptor (sTCR), which comprises (i) all or part of a TCR α chain, except the transmembrane domain thereof, and (ii) all or part of a TCR β chain, except the transmembrane domain thereof, wherein (i) and (ii) each comprise a functional variable domain and at least a part of the constant domain of the TCR chain, and are linked by a disulphide bond between constant domain residues which is not present in native TCR, Characterised in that the sTCR recognises a CD1-antigen complex, a bacterial superantigen or a peptide-MHC/superantigen complex.

In another aspect, the invention provides a soluble αβ-form T cell receptor (sTCR) which recognises a CD1-antigen complex, a bacterial superantigen or a peptide-MHC/superantigen complex, wherein a covalent disulphide bond links a residue of the immunoglobulin region of the constant domain of the α chain to a residue of the immunoglobulin region of the constant domain of the β chain.

The sTCRs of the present invention have the advantage that they do not contain heterologous polypeptides which may be immunogenic, or which may result in the sTCR being cleared quickly from the body. Furthermore, TCRs of the present invention have a three-dimensional structure which is highly similar to the native TCRs from which they are derived and, due to this structural similarity, they are not likely to be immunogenic.

TCRs of the present invention are soluble. In the context of this application, solubility is defined as the ability of the TCR to be purified as a mono disperse heterodimer in phosphate buffered saline (PBS) (KCL 2.7 mM, $KH_2PO_4$ 1.5 mM, NaCl 137 mM and $Na_2PO4$ 8 mM, pH 7.1-7.5. Life Technologies, Gibco BRL) at a concentration of 1 mg/ml and for >90% of said TCR to remain as a mono disperse heterodimer after incubation at 25° C. for 1 hour. In order to assess the solubility of the TCR, it is first purified as described in Example 2. Following this purification, 100 μg of the TCR is analysed by analytical size exclusion chromatography e.g. using a Pharmacia Superdex 75 HR column equilibrated in PBS. A further 100 μg of the TCR is incubated at 25° C. for 1 hour and then analysed by size exclusion chromatography as before. The size exclusion traces are then analysed by integration and the areas under the peaks corresponding to the mono disperse heterodimer are compared. The relevant peaks may be identified by comparison with the elution position of protein standards of known molecular weight. The mono disperse heterodimeric soluble TCR has a molecular weight of approximately 50 kDa. As stated above, the TCRs of the present invention are soluble. However, as explained in more detail below, the TCRs can be coupled to a moiety such that the resulting complex is insoluble, or they may be presented on the surface of an insoluble solid support.

The numbering of TCR amino acids used herein follows the IMGT system described in The T Cell Receptor Factsbook, 2001, LeFranc & LeFranc, Academic Press. In this system, the α chain constant domain has the following notation: TRAC*01, where "TR" indicates T Cell Receptor gene; "A" indicates α chain gene; C indicates constant region; and "*01" indicates allele 1. The β chain constant domain has the following notation: TRBC1*01. In this instance, there are two possible constant region genes "C1" and "C2". The translated domain encoded by each allele can be made up from the genetic code of several exons; therefore these are also specified. Amino acids are numbered according to the exon of the particular domain in which they are present.

The extracellular portion of native TCR consists of two polypeptides (αβ or γδ) each of which has a membrane-proximal constant domain, and a membrane-distal variable domain (see FIG. 1). Each of the constant and variable domains includes an intra-chain disulphide bond. The variable domains contain the highly polymorphic loops analogous to the complementarity determining regions (CDRs) of antibodies. CDR3 of the TCR interacts with the peptide presented by MHC, and CDRs 1 and 2 interact with the peptide and the MHC. The diversity of TCR sequences is generated via somatic rearrangement of linked variable (V), diversity (D), joining (J), and constant genes. Functional α chain polypeptides are formed by rearranged V-J-C regions, whereas β chains consist of V-D-J-C regions. The extracellular constant domain has a membrane proximal region and an immunoglobulin region. The membrane proximal region consists of the amino acids between the transmembrane domain and the membrane proximal cysteine residue. The constant immunoglobulin domain consists of the remainder of the constant domain amino acid residues, extending from the membrane proximal cysteine to the beginning of the joining region, and is characterised by the presence of an immunoglobulin-type fold. There is a single a chain constant domain, known as Cα1 or TRAC*01, and two different β constant domains, known as Cβ1 or TRBC1*01 and Cβ2 or TRBC2*01. The difference between these different β constant domains is in respect of amino acid residues 4, 5 and 37 of exon 1. Thus, TRBC1*01 has 4N, 5K and 37 in exon 1 thereof, and TRBC2*01 has 4K, 5N and 37Y in exon 1 thereof. The extent of each of the TCR extracellular domains is somewhat variable.

In the present invention, the disulphide bond is introduced between residues located in the constant domains (or parts thereof) of the respective chains. The respective chains of the TCR comprise sufficient of the variable domains thereof to be able to interact with its TCR ligand counterpart (CD1-antigen complex, superantigen or superantigen/pMHC complex)—if it binds. Such interactions can be measured using a BIAcore 3000™ or BIAcore 2000™ instrument. WO99/6120 provides detailed descriptions of the methods required to analyse TCR binding to MHC-peptide complexes and these methods are equally applicable to the study of TCR/CD1 and TCR/superantigen interactions. In order to apply these methods to the study of TCR/CD1 interactions soluble forms of CD1 are required, the production of which are described in (Bauer (1997) Eur J Immunol 27 (6) 1366-1373).

In one embodiment, the respective chains of the sTCR of the invention also comprise the intra-chain disulphide bonds thereof. The TCR of the present invention may comprise all of the extracellular constant Ig region of the respective TCR chains, and preferably all of the extracellular domain of the respective chains, i.e. including the membrane proximal region. In native TCR, there is a disulphide bond linking the conserved membrane proximal regions of the respective chains. In one embodiment of the present invention, this disulphide bond is not present. This may be achieved by mutating the appropriate cysteine residues (amino acid 4, exon 2 of the TRAC*01 gene and amino acid 2 of both the TRBC1*01 and TRBC2*01 genes respectively) to another amino acid, or truncating the respective chains so that the cysteine residues are not included. A preferred soluble TCR according to the invention comprises the native α and β TCR chains truncated at the C-terminus such that the cysteine residues which form the native interchain disulphide bond are excluded, i.e. truncated at the residue 1, 2, 3, 4, 5, 6, 7, 8, 9 or 10 residues N-terminal to the cysteine residues. It is to be noted however that the native inter-chain disulphide bond may be present in TCRs of the present invention, and that, in certain embodiments, only one of the TCR chains has the native cysteine residue which forms the native interchain disulphide bond. This cysteine can be used to attach moieties to the TCR.

However, the respective TCR chains may be shorter. Because the constant domains are not directly involved in contacts with the peptide-MEC ligands, the C-terminal truncation point may be altered substantially without loss of functionality.

Alternatively, a larger fragment of the constant domains may be present than is preferred herein, i.e. the constant domains need not be truncated just prior to the cysteines forming the interchain disulphide bond. For instance, the entire constant domain except the transmembrane domain (i.e. the extracellular and cytoplasmic domains) could be included. It may be advantageous in this case to mutate one or more of the cysteine residues forming the interchain disulphide bond in the cellular TCR to another amino acid residue which is not involved in disulphide bond formation, or to delete one or more of these residues.

The signal peptide may be omitted if the soluble TCR is to be expressed in prokaryotic cells, for example E. coli, since it does not serve any purpose in the mature TCR for its ligand binding ability, and may in some circumstances prevent the formation of a functional soluble TCR. In most cases, the cleavage site at which the signal peptide is removed from the mature TCR chains is predicted but not experimentally determined. Engineering the expressed TCR chains such that they are a few, i.e. up to about 10 for example, amino acids longer or shorter at the N-terminal end may have no significance for the functionality (i.e. the ability to recognise CD1) of the soluble TCR. Certain additions which are not present in the original protein sequence could be added. For example, a short tag sequence which can aid in purification of the TCR chains could be added, provided that it does not interfere with the correct structure and folding of the antigen binding site of the TCR.

For expression in E. coli, a methionine residue may be engineered onto the N-terminal starting point of the predicted mature protein sequence in order to enable initiation of translation.

Far from all residues in the variable domains of TCR chains are essential for antigen specificity and functionality. Thus, a significant number of mutations can be introduced in this domain without affecting antigen specificity and functionality. Far from all residues in the constant domains of TCR chains are essential for antigen specificity and functionality. Thus, a significant number of mutations can be introduced in this region without affecting antigen specificity.

The TCR β chain contains a cysteine residue which is unpaired in the cellular or native TCR. It is preferred if this cysteine residue is removed or mutated to another residue to avoid incorrect intrachain or interchain pairing. Substitutions of this cysteine residue for another residue, for example serine or alanine, can have a significant positive effect on refolding efficiencies in vitro.

The disulphide bond may be formed by mutating non-cysteine residues on the respective chains to cysteine, and causing the bond to be formed between the mutated residues. Residues whose respective β carbons are approximately 6 Å (0.6 nm) or less, and preferably in the range 3.5 Å (0.35 nm) to 5.9 Å (0.59 nm) apart in the native TCR are preferred, such that a disulphide bond can be formed between cysteine residues introduced in place of the native residues. It is preferred if the disulphide bond is between residues in the constant immunoglobulin region, although it could be between residues of the membrane proximal region. Preferred sites where cysteines can be introduced to form the disulphide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 48 | Ser 57 | 0.473 |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

One sTCR of the present invention is derived from the A6 Tax TCR (Garboczi et al, Nature, 1996, 384(6605): 134-141). In one embodiment, the sTCR comprises the whole of the TCR α chain which is N-terminal of exon 2, residue 4 of TRAC*01 (amino acid residues 1-182 of the α chain according to the numbering used in Garboczi et al) and the whole of the TCR β chain which is N-terminal of exon 2, residue 2 of both TRBC1*01 and TRCB2*01 (amino acid residues 1-210 of the β chain according to the numbering used in Garboczi et al). In order to form the disulphide bond, threonine 48 of exon 1 in TRAC*-01 (threonine 158 of the α chain according to the numbering used in Garboczi et al) and serine 57 of exon 1 in both TRBC1*01 and TRBC2*01 (serine 172 of the 0 chain according to the numbering used in Garboczi et al) may each be mutated to cysteine. These amino acids are located in β strand D of the constant domain of α and β TCR chains respectively.

It is to be noted that, in FIGS. 3a and 3b, residue 1 (according to the numbering used in Garboczi et al) is K and N respectively. The N-terminal methionine residue is not present in native A6 Tax TCR and, as mentioned above, is sometimes present when the respective chains are produced in bacterial expression systems.

Now that the residues in human TCRs which can be mutated into cysteine residues to form a new interchain disulphide bond have been identified, those of skill in the art will be able to mutate any TCR in the same way to produce a soluble form of that TCR having a new interchain disulphide bond. In humans, the skilled person merely needs to look for the following motifs in the respective TCR chains to identify the residue to be mutated (the shaded residue is the residue for mutation to a cysteine).

| α Chain Thr 48: | DSDVYITDKTVLDMRSMDFK (amino acids 39-58 of exon 1 of the TRAC*01 gene) (SEQ ID 1) |
| α Chain Thr 45: | QSKDSDVYITDKTVLDMRSM (amino acids 36-55 of exon 1 of the TRAC*01 gene) (SEQ ID 2) |
| α Chain Tyr 10: | DIQNPDPAVYQLRDSKSSDK (amino acids 1-20 of exon 1 of the TRAC*01 gene) (SEQ ID 3) |
| α Chain Ser 15: | DPAVYQLRDSKSSDKSVCLF (amino acids 6-25 of exon 1 of the TRAC*01 gene) (SEQ ID 4) |
| β Chain Ser 57: | NGKEVHSGVSTDPQPLKEQP (amino acids 48-67 of exon 1 of the TRBC1*01 & TRBC2*01 genes) (SEQ ID 5) |
| β Chain Ser 77: | ALNDSRYALSSRLRVSATFW (amino acids 68-87 of exon 1 of the TRBC1*01 & TRBC2*01 genes) (SEQ ID 6) |
| β Chain Ser 17: | PPEVAVFEPSEAEISHTQKA (amino acids 8-27 of exon 1 of the TRBC1*01 & TRBC2*01 genes) (SEQ ID 7) |
| β Chain Asp 59: | KEVHSGVSTDPQPLKEQPAL (amino acids 50-69 of exon 1 of the TRBC1*01 & TRBC2*01 genes gene) (SEQ ID 8) |
| β Chain Glu 15: | VFPPEVAVFEPSEAEISHTQ (amino acids 6-25 of exon 1 of the TRBC1*01 & TRBC2*01 genes) (SEQ ID 9) |

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, ClustalW, available on the European Bioinformatics Institute website (http://www.ebi.ac.uk/index.html) can be used to compare the motifs above to a particular TCR chain sequence in order to locate the relevant part of the TCR sequence for mutation.

The present invention includes within its scope human disulphide-linked αβ TCRs, as well as disulphide-linked αβ TCRs of other mammals, including, but not limited to, mouse, rat, pig, goat and sheep. As mentioned above, those of skill in the art will be able to determine sites equivalent to the above-described human sites at which cysteine residues can be introduced to form an inter-chain disulphide bond. For example, the following shows the amino acid sequences of the mouse Cα and Cβ soluble domains, together with motifs showing the murine residues equivalent to the human residues mentioned above that can be mutated to cysteines to form a TCR interchain disulphide bond (where the relevant residues are shaded):

Mouse Cα soluble domain:
(SEQ ID 10)
PYIQNPEPAVYQLKDPRSQDST
LCLFTDFDSQINVPKTMESGTF
ITDKTVLDMKAMDSKSNGAIAW
SNQTSFTCQDIFKETNATYPSS
DVP Mouse Cβ soluble domain:
(SEQ ID 11)
EDLRNVTPPKVSLFEPSKAEIA
NKQKATLVCLARGFFPDHVELS
WWVNGREVHSGVSTDPQAYKES
NYSYCLSSRLRVSATFWHNPRN
HFRCQVQFHGLSEEDKWPEGSP
KPVTQNISAEAWGRAD Murine equivalent of human α Chain Thr 48:
(SEQ ID 12)
ESGTFITDKTVLDMKAMDSK Murine equivalent of human α Chain Thr 45:
(SEQ ID 13)
KTMESGTFTDKTVLDMKAM Murine equivalent of human α Chain Tyr 10:
(SEQ ID 14)
YIQNPEPAVYQLKDPRSQDS -continued

```
                                                          (SEQ ID 15)
Murine equivalent of human α Chain Ser 15:  AVYQLKDPRSĊDSTLCLFTD (SEQ ID 16)
Murine equivalent of human β Chain Ser 57:  NGREVHSGVSĊDPQAYKESN (SEQ ID 17)
Murine equivalent of human β Chain Ser 77:  KESNYSYCLSĊRLRVSATFW (SEQ ID 18)
Murine equivalent of human β Chain Ser 17:  PPKVSLFEPĊKAEIANKQKA (SEQ ID 19)
Murine equivalent of human β Chain Asp 59:  REVHSGVSTDĊQAYKESNYS (SEQ ID 20)
Murine equivalent of human β Chain Glu 15:  VTPPKVSLFEPSKAEIANKQ
```

In a preferred embodiment of the present invention, (i) and (ii) of the TCR each comprise the functional variable domain of a first TCR fused to all or part of the constant domain of a second TCR, the first and second TCRs being from the same species and the inter-chain disulphide bond being between residues in said respective all or part of the constant domain not present in native TCR. In one embodiment, the first and second TCRs are human. In other words, the disulphide bond-linked constant domains act as a framework on to which variable domains can be fused. The resulting TCR will be substantially identical to the native TCR from which the first TCR is obtained. Such a system allows the easy expression of any functional variable domain on a stable constant domain framework.

The constant domains of the A6 Tax sTCR described above, or indeed the constant domains of any of the mutant αβ TCRs having a new interchain disulphide bond described above, can be used as framework onto which heterologous variable domains can be fused. It is preferred if the fusion protein retains as much of the conformation of the heterologous variable domains as possible. Therefore, it is preferred that the heterologous variable domains are linked to the constant domains at any point between the introduced cysteine residues and the N terminus of the constant domain. For the A6 Tax TCR, the introduced cysteine residues on the a and θ chains are preferably located at threonine 48 of exon 1 in TRAC*01 (threonine 158 of the α chain according to the numbering used in Garboczi et al) and serine 57 of exon 1 in both TRBC1*01 and TRBC2*01 (serine 172 of the β chain according to the numbering used in Garboczi et al) respectively. Therefore it is preferred if the heterologous α and β chain variable domain attachment points are between residues 48 (159 according to the numbering used in Garboczi et al) or 58 (173 according to the numbering used in Garboczi et al) and the N terminus of the α or β constant domains respectively.

The residues in the constant domains of the heterologous α and β chains corresponding to the attachment points in the A6 Tax TCR can be identified by sequence homology. The fusion protein is preferably constructed to include all of the heterologous sequence N-terminal to the attachment point.

As is discussed in more detail below, the sTCR of the present invention may be derivatised with, or fused to, a moiety at its C or N terminus. The C terminus is preferred as this is distal from the binding domain. In one embodiment, one or both of the TCR chains have a cysteine residue at its C and/or N terminus to which such a moiety can be fused.

A soluble TCR (which is preferably human) of the present invention may be provided in substantially pure form, or as a purified or isolated preparation. For example, it may be provided in a form which is substantially free of other proteins.

A plurality of soluble TCRs of the present invention may be provided in a multivalent complex. Thus, the present invention provides, in one aspect, a multivalent T cell receptor (TCR) complex, which comprises a plurality of soluble T cell receptors as described herein. Each of the plurality of soluble TCRs is preferably identical.

In another aspect, the invention provides a method for detecting a TCR ligand selected from CD1-antigen complexes, bacterial superantigens, and MHC-peptide/superantigen complexes which method comprises:
 (i) providing a soluble T cell receptor or a multivalent T cell receptor complex as described herein;
 (ii) contacting the soluble T cell receptor or multivalent TCR complex with the TCR ligand; and
 (iii) detecting binding of the soluble T cell receptor or multivalent TCR complex to the TCR ligand.

In the multivalent complex of the present invention, the TCRs may be in the form of multimers, and/or may be present on or associated with a lipid bilayera, for example, a liposome.

In its simplest form, a multivalent TCR complex according to the invention comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Structures which are a good deal larger than TCR tetramers may be used in tracking or targeting cells expressing CD1-antigen complexes. Preferably the structures are in the range 10 nm to 10 μm in diameter. Each structure may display multiple TCR molecules at a sufficient distance apart to enable two or more TCR molecules on the structure to bind simultaneously to two or more CD1-antigen complexes on a cell and thus increase the avidity of the multimeric binding moiety for the cell.

Suitable structures for use in the invention include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present invention. For example, the label or other moiety may be included in a mixed molecule multimer. An example of such a multimeric molecule is a tetramer containing three TCR molecules and one peroxidase molecule. This could be achieved by mixing the TCR and the enzyme at a molar ratio of 3:1 to generate tetrameric complexes, and isolating the desired complex from any complexes not containing the correct ratio of molecules. These mixed molecules could contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

Alternative means of biotinylating the TCR may be possible. For example, chemical biotinylation may be used. Alternative biotinylation tags may be used, although certain amino acids in the biotin tag sequence are essential (Schatz, (1993). *Biotechiology N Y* 11(10): 1138-43). The mixture used for biotinylation may also be varied. The enzyme requires Mg-ATP and low ionic strength, although both of these conditions may be varied e.g. it may be possible to use a higher ionic strength and a longer reaction time. It may be possible to use a molecule other than avidin or streptavidin to form multimers of the TCR. Any molecule which binds biotin in a multivalent manner would be suitable. Alternatively, an entirely different linkage could be devised (such as polyhistidine tag to chelated nickel ion (Quiagen Product Guide 1999, Chapter 3 "Protein Expression, Purification, Detection and Assay" p. 35-37). Preferably, the tag is located towards the C-terminus of the protein so as to minimise the amount of steric hindrance in the interaction with the counterpart TCR ligand.

One or both of the TCR chains may be labelled with a detectable label, for example a label which is suitable for diagnostic purposes. Thus, the invention provides a method for detecting a TCR ligand selected from CD1-antigen complexes, bacterial superantigens, and MHC-peptide/superantigen complexes which method comprises contacting the TCR ligand with a TCR or multimeric TCR complex in accordance with the invention which is specific for the TCR ligand; and detecting binding of the TCR or multimeric TCR complex to the TCR ligand. In tetrameric TCR formed using biotinylated heterodimers, fluorescent streptavidin (commercially available) can be used to provide a detectable label. A fluorescently-labelled tetramer is suitable for use in FACS analysis, for example to detect antigen presenting cells carrying the peptide for which the TCR is specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant regions of the α and β chain, respectively.

The TCR (or multivalent complex thereof) of the present invention may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present invention may have enhanced binding capability for a TCR ligand compared to a non-multimeric T cell receptor heterodimer. Thus, the multivalent TCR complexes according to the invention are particularly useful for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the TCR ligand and having the therapeutic agent associated therewith.

In particular, the soluble TCR or multivalent TCR complex can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to T cell receptors or multivalent TCR complexes specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
 small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;
 peptide cytotoxins, i.e. proteins or fragments thereof with the ability to kill mammalian cells. Examples include ricin, diphtheria toxin, pseudomonas bacterial exotoxin A, DNAase and RNAase;
 radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213;

prodrugs, such as antibody directed enzyme pro-drugs;

immuno-stimulants, i.e. moieties which stimulate immune response. Examples include cytokines such as IL-2, chemokines such as IL-8, platelet factor 4, melanoma growth stimulatory protein, etc, antibodies or fragments thereof such as anti-CD3 antibodies or fragments thereof, complement activators, xenogeneic protein domains, allogeneic protein domains, viral/bacterial protein domains and viral/bacterial peptides.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

A multitude of disease treatments can potentially be enhanced by localising the drug through the specificity of soluble TCRs.

Viral diseases for which drugs exist, e.g. HIV, SIV, EBV, CMV, would benefit from the drug being released or activated in the near vicinity of infected cells. For cancer, the localisation in the vicinity of tumours or metastasis would enhance the effect of toxins or immunostimulants. In autoimmune diseases, immunosuppressive drugs could be released slowly, having more local effect over a longer time-span while minimally affecting the overall immuno-capacity of the subject. In the prevention of graft rejection, the effect of immunosuppressive drugs could be optimised in the same way. For vaccine delivery, the vaccine antigen could be localised in the vicinity of antigen presenting cells, thus enhancing the efficacy of the antigen. The method can also be applied for imaging purposes.

The soluble TCRs of the present invention may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

The use of the soluble TCRs and/or multivalent TCR complexes of the present invention in the preparation of a composition for the treatment of cancer or autoimmune disease is also envisaged.

Also provided is a method of treatment of cancer or autoimmune disease comprising administration to a patient in need thereof of an effective amount of the soluble TCRs and/or multivalent TCR complexes of the present invention.

As is common in anti-cancer and autoimmune therapy the sTCRs of this invention maybe used in combination with other agents for the treatment of cancer and autoimmune disease, and other related conditions found in similar patient groups.

Medicaments in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions. Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986). Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas. Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurised aerosols, nebulizers or insufflators. Pharmaceutical compositions adapted for vaginal administration may be presented as pessaries, tampons, creams, gels, pastes, foams or spray formulations. Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substances of the present invention can vary between wide limits, depending upon the disease or disorder to be treated, the age and condition of the individual to be treated, etc. and a physician will ultimately determine appropriate dosages to be used. The dosage may be repeated as often as appropriate. If side effects develop the amount and/or frequency of the dosage can be reduced, in accordance with normal clinical practice.

Gene cloning techniques may be used to provide a sTCR of the invention, preferably in substantially pure form. These techniques are disclosed, for example, in J. Sambrook et al *Molecular Cloning* 2nd Edition, Cold Spring Harbor Laboratory Press (1989). Thus, in a further aspect, the present invention provides a nucleic acid molecule comprising a sequence encoding a chain of the soluble TCR of the present invention, or a sequence complementary thereto. Such nucleic acid sequences may be obtained by isolating TCR-encoding nucleic acid from T-cell clones and making appropriate mutations (by insertion, deletion or substitution).

The nucleic acid molecule may be in isolated or recombinant form. It may be incorporated into a vector and the vector may be incorporated into a host cell. Such vectors and suitable hosts form yet further aspects of the present invention.

The invention also provides a method for obtaining a TCR chain, which method comprises incubating such a host cell under conditions causing expression of the TCR chain and then purifying the polypeptide.

The soluble TCRs of the present invention may obtained by expression in a bacterium such as *E. coli* as inclusion bodies, and subsequent refolding in vitro.

Refolding of the TCR chains may take place in vitro under suitable refolding conditions. In a particular embodiment, a TCR with correct conformation is achieved by refolding solubilised TCR chains in a refolding buffer comprising a solubilising agent, for example urea. Advantageously, the urea may be present at a concentration of at least 0.1M or at least 1M or at least 2.5M, or about 5M. An alternative solubilising agent which may be used is guanidine, at a concentration of between 0.1M and 8M, preferably at least 1M or at least 2.5M. Prior to refolding, a reducing agent is preferably employed to ensure complete reduction of cysteine residues. Further denaturing agents such as DTT and guanidine may be used as necessary. Different denaturants and reducing agents may be used prior to the refolding step (e.g. urea, β-mercaptoethanol). Alternative redox couples may be used during refolding, such as a cystamine/cysteamine redox couple, DTT or β-mercaptoethanol/atmospheric oxygen, and cysteine in reduced and oxidised forms.

Folding efficiency may also be increased by the addition of certain other protein components, for example chaperone proteins, to the refolding mixture. Improved refolding has been achieved by passing protein through columns with immobilised mini-chaperones (Altamirano, et al. (1999). *Nature Biotechnology* 17: 187-191; Altamirano, et al. (1997). *Proc Natl Acad Sci USA* 94(8): 3576-8).

Alternatively, soluble TCRs of the present invention may be obtained by expression in a eukaryotic cell system, such as insect cells. For, example co-pending application (WO 03/020763) discloses expression of peptide-MHC-binding soluble TCRs of the same basic design to those of the present invention to be expressed in yeast and insect cells, and, expression in a wide range of other prokaryotic or eukaryotic systems is to be expected. Thus, there are a number of mammalian expression systems that have been used for the production of membrane-bound TCRs. For example, one study (Rubinstein (2003) *J. Immunol* 170 (3) 1209-1217) demonstrates the successful in vitro retro-virus mediated transduction of mature T cells with DNA encoding a non-native, membrane-bound TCR. This led to the production of T cells capable of specifically killing APCs that expressed the pMHC complex recognised by the introduced TCR. A further study (Pogulis (1998) *Hum Gene Ther* 9 (15) 2285-2297) used a retro-viral system to transduce murine bone marrow cells with TCR genes. The transduced bone marrow cells were then introduced into mice and expression of the introduced TCR was demonstrated.

It is also anticipated that TCRs of the present invention would be amenable to expression into the milk of transgenic animals including but not limited to mice, rats, cows, sheep, and goats using similar methods to those previously demonstrated for antibody production. For example, (Sola (1998) *J Virol* 72 (5) 3762-3772) describes the introduction of DNA encoding a chimeric antibody (IgA) into mice and demonstrates that mice capable of secreting the introduced IgA into their milk could be produced.

Purification of the expressed TCR may be achieved by many different means that can be tailored to the particular milieu into which the TCR is expressed. Alternative modes of ion exchange may be employed or other modes of protein purification may be used such as gel filtration chromatography or affinity chromatography.

Soluble TCRs and multivalent TCR complexes of the present invention also find use in screening for agents, such as small chemical compounds, which have the ability to inhibit the binding of the TCR to its TCR ligand. Thus, in a further aspect, the present invention provides a method for screening for an agent which inhibits the binding of a T cell receptor to a a TCR ligand selected from CD1-antigen complexes, bacterial superantigens, and MHC-peptide/superantigen complexes, comprising monitoring the binding of a soluble T cell receptor of the invention with a TCR ligand in the presence of an agent; and selecting agents which inhibit such binding.

Suitable techniques for such a screening method include the Surface Plasmon Resonance-based method described in WO 01/22084. Other well-known techniques that could form the basis of this screening method are Scintillation Proximity Analysis (SPA) and Amplified Luminescent Proximity Assay.

Agents selected by screening methods of the invention can be used as drugs, or as the basis of a drug development programme, being modified or otherwise improved to have characteristics making them more suitable for administration as a medicament. Such medicaments can be used for the treatment of conditions which include an unwanted T cell response component. Such conditions include cancer (e.g. renal, ovarian, bowel, head & neck, testicular, lung, stomach, cervical, bladder, prostate or melanoma), autoimmune disease, graft rejection and graft versus host disease.

Preferred features of each aspect of the invention are as for each of the other aspects *mutatis mutandis*. The prior art documents mentioned herein are incorporated to the fullest extent permitted by law.

EXAMPLES

The invention is further described in the following examples, which do not limit the scope of the invention in any way.

Reference is made in the following to the accompanying drawings.

Example 1

Design of Primers and Mutagenesis of a CD1-Binding TCR α and β Chains

For mutating a CD1-binding TCR threonine 48 of exon 1 in TRAC*01 to cysteine, the following primers were designed (mutation shown in lower case):

```
5'-C ACA GAC AAA tgT GTG CTA GAC AT    (SEQ ID 21)

5'-AT GTC TAG CAC Aca TTT GTC TGT G    (SEQ ID 22)
```

For mutating CD1-binding TCR serine 57 of exon 1 in both TRBC1*01 and TRBC2*01 to cysteine, the following primers were designed (mutation shown in lower case):

```
5'-C AGT GGG GTC tGC ACA GAC CC    (SEQ ID 23)

5'-GG GTC TGT GCa GAC CCC ACT G    (SEQ ID 24)
```

PCR Mutagenesis:

Expression plasmids containing the genes for the CD1-binding TCR were obtained from cDNA isolated from a CD1 specific CD1 T cell clone. The TCR α or β chain were mutated using the α-chain primers or the β-chain primers respectively, as follows. 100 ng of plasmid was mixed with 5 µl 10 mM dNTP, 25 µl 10×Pfu-buffer (Stratagene), 10 units Pfu polymerase (Stratagene) and the final volume was adjusted to 240 µl with $H_2O$. 48 µl of this mix was supplemented with primers diluted to give a final concentration of 0.2 µM in 50 µl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 µl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University. The respective mutated nucleic acid and amino acid sequences are shown in FIGS. 2a and 3a for the α chain and FIGS. 2b and 3b for the β chain.

Example 2

Expression, Refolding and Purification of Soluble TCR

The expression plasmids containing the mutated α-chain and β-chain respectively were transformed separately into *E. coli* strain BL21pLysS, and single ampicillin-resistant colonies were grown at 37° C. in TYP (ampicillin 100 µg/ml) medium to $OD_{600}$ of 0.4 before inducing protein expression with 0.5 mM IPTG. Cells were harvested three hours post-induction by centrifugation for 30 minutes at 400 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Approximately 120 mg (i.e. 4 µmole) of solubilised α chain inclusion body, and 30 mg (i.e. 1 µmole) of solubilised α chain inclusion body was thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer:

100 mM Tris pH 8.5, 400 mM L-Arginine, 2 mM EDTA, 5 mM reduced Glutathione, 0.5 mM oxidised Glutathione, 5M urea, 0.2 mM PMSF. The solution was left for 24 hrs. The refold was then dialysed twice, firstly against 10 liters of 10 mM urea, secondly against 10 liters of 10 mM urea, 10 mM Tris pH 8.0. Both refolding and dialysis steps were carried out at 6-8° C.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4° C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50

Example 3

BIAcore Surface Plasmon Resonance Characterisation of sTCR Binding to CD1

A surface plasmon resonance biosensor (BIAcore 3000™ was used to analyse the binding of a sTCR to its CD1 ligand. This was facilitated by producing soluble CD1 complexes as described in (Bauer (1997) Eur J Immunol 27 (6) 1366-1373) which were immobilised to a streptavidin-coated binding surface in a semi-oriented fashion, allowing efficient testing of the binding of a soluble T-cell receptor to up to four different TCR ligands (immobilised on separate flow cells) simultaneously. Manual injection of HLA complex allows the precise level of immobilised TCR ligand to be manipulated easily.

Such immobilised complexes are capable of binding both T-cell receptors and the coreceptor CD8αα both of which may be injected in the soluble phase. Specific binding of TCR is obtained even at low concentrations (at least 40 μg/ml), implying the TCR is relatively stable. The CD1 binding binding properties of sTCR are observed to be qualitatively and quantitatively similar if sTCR is used either in the soluble or immobilised phase. This is an important control for partial activity of soluble species and also suggests that biotinylated CD1 complexes are biologically as active as non-biotinylated complexes.

The interactions between the CD1-binding sTCR containing a novel inter-chain bond and soluble CD1 were analysed on a BIAcore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the CD1 complexes in separate flow cells. The assay was then performed by passing sTCR over the surfaces of the different flow cells at a constant flow rate, measuring the SPR response in doing so. Injections of soluble sTCR at constant flow rate and different concentrations over the soluble CD1 complex were used to define the background resonance.

The Kd value obtained for the interaction between the CD1-binding TCR and soluble CD1 was 6.0±0.3 μM)

The invention claimed is:

1. A soluble T cell receptor (sTCR), which comprises (i) all or part of a TCR α chain, except the transmembrane domain thereof, and (ii) all or part of a TCR β chain, except the transmembrane domain thereof, wherein (i) and (ii) each comprise a variable domain and at least a part of the constant domain of the TCR chain, and are linked by a disulphide bond between constant domain cysteine residues substituted for Thr 48 of exon 1 of TRAC*01 and Ser 57 of exon 1 of TRBC1*01 or TRBC2*01, wherein Thr 48 is amino acid 10 of SEQ ID NO:1 and wherein Ser 57 is amino acid 10 of SEQ ID NO:5 characterized in that the sTCR binds a CD1-antigen complex, wherein one or both of (i) and (ii) comprise all of the extracellular constant immunoglobulin domain of the TCR chain.

2. A sTCR as claimed in claim 1, wherein one or both of (i) and (ii) comprise all of the extracellular domain of the TCR chain.

3. A sTCR as claimed in claim 1, wherein an interchain disulphide bond in native TCR is not present.

4. A sTCR as claimed in claim 3, wherein native α and β TCR chains are truncated at the C-terminus such that the cysteine residues which form the native interchain disulphide bond are excluded.

5. A sTCR as claimed in claim 3, wherein cysteine residues which form the native interchain disulphide bond are substituted to another residue.

6. A sTCR as claimed in claim 5, wherein cysteine residues which form the native interchain disulphide bond are substituted to serine or alanine.

7. A sTCR as claimed in claim 1, wherein an unpaired cysteine residue present in native TCR β chain is not present.

8. A sTCR as claimed in claim 1, wherein (i) and (ii) each comprise the variable domain of a first TCR fused to all or part of the constant domain of a second TCR, the first and second TCRs being from the same species.

9. A sTCR as claimed in claim 1, wherein one or both of the chains are fused to a moiety at its C or N terminus.

10. A sTCR as claimed in claim 1, wherein one or both of the chains have a cysteine residue at its C and/or N terminus to which a moiety can be fused.

11. A sTCR as claimed in claim 1, further comprising a detectable label.

12. A sTCR as claimed in claim 1 associated with a therapeutic agent.

13. A multivalent T cell receptor (TCR) complex comprising a plurality of sTCRs as claimed in claim 1.

14. A complex as claimed in claim 13, comprising a sTCR multimer.

15. A complex as claimed in claim 14, wherein the sTCR multimer comprises two or three or four or more sTCRs associated with one another.

16. A complex as claimed in claim 13, wherein the sTCRs or sTCR multimers are present in a lipid bilayer or are attached to a particle.

17. A method for detecting CD1-antigen complexes, which comprises:
 (i) providing a soluble TCR as claimed in claim 1 or a multivalent T cell receptor complex comprising a plurality of sTCRs as claimed in claim 1;
 (ii) contacting the soluble TCR or multivalent TCR complex with the CD-1antigen complexes; and
 (iii) detecting binding of the soluble TCR or multivalent TCR complex to the CD-1 antigen complexes.

18. A pharmaceutical formulation comprising a sTCR as claimed in claim 1, and/or a multivalent TCR complex comprising a plurality of sTCRs as claimed in claim 1, together with a pharmaceutically acceptable carrier.

19. The complex of claim 15 wherein the sTCRs are associated with one another via a linker molecule.

* * * * *

```
                        SEQUENCE LISTING

<160> NUMBER OF SEQ ID NOS: 28

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR alpha chain

<400> SEQUENCE: 1

Asp Ser Asp Val Tyr Ile Thr Asp Lys Thr Val Leu Asp Met Arg Ser
1               5                   10                  15

Met Asp Phe Lys
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR alpha chain

<400> SEQUENCE: 2

Gln Ser Lys Asp Ser Asp Val Tyr Ile Thr Asp Lys Thr Val Leu Asp
1               5                   10                  15

Met Arg Ser Met
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR alpha chain

<400> SEQUENCE: 3
```

```
Asp Ile Gln Asn Pro Asp Pro Ala Val Tyr Gln Leu Arg Asp Ser Lys
1               5                   10                  15

Ser Ser Asp Lys
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR alpha chain

<400> SEQUENCE: 4

Asp Pro Ala Val Tyr Gln Leu Arg Asp Ser Lys Ser Ser Asp Lys Ser
1               5                   10                  15

Val Cys Leu Phe
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 5

Asn Gly Lys Glu Val His Ser Gly Val Ser Thr Asp Pro Gln Pro Leu
1               5                   10                  15

Lys Glu Gln Pro
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 6

Ala Leu Asn Asp Ser Arg Tyr Ala Leu Ser Ser Arg Leu Arg Val Ser
1               5                   10                  15

Ala Thr Phe Trp
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 7

Pro Pro Glu Val Ala Val Phe Glu Pro Ser Glu Ala Glu Ile Ser His
1               5                   10                  15

Thr Gln Lys Ala
            20

<210> SEQ ID NO 8
<211> LENGTH: 20
<212> TYPE: PRT
<213> ORGANISM: Artificial Sequence
```

```
<220> FEATURE:
<223> OTHER INFORMATION: Description of Artificial Sequence:  partial
      synthetic TCR beta chain

<400> SEQUENCE: 8

Lys Glu Val His Ser Gly Val Ser Thr Asp Pro Gln Pro Leu Lys Glu
1               5                   10                  15

Gln Pro Ala Leu
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence:  partial
      synthetic TCR beta chain

<400> SEQUENCE: 9

Val Phe Pro Pro Glu Val Ala Val Phe Glu Pro Ser Glu Ala Glu Ile
1               5                   10                  15

Ser His Thr Gln
            20

<210> SEQ ID NO 10
<211> LENGTH: 91
<212> TYPE: PRT
<213> ORGANISM: Mouse

<400> SEQUENCE: 10

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
                20                  25                  30

Ile Asn Val Pro Lys Thr Met Glu Ser Gly Thr Phe Ile Thr Asp Lys
            35                  40                  45

Thr Val Leu Asp Met Lys Ala Met Asp Ser Lys Ser Asn Gly Ala Ile
        50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro
                85                  90

<210> SEQ ID NO 11
<211> LENGTH: 126
<212> TYPE: PRT
<213> ORGANISM: Mouse

<400> SEQUENCE: 11

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Arg Glu Val His Ser Gly Val Ser Thr Asp Pro Gln Ala Tyr Lys
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
```

-continued

```
                85                  90                  95
His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
        115                 120                 125

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence:  partial
      synthetic TCR alpha chain

<400> SEQUENCE: 12

Glu Ser Gly Thr Phe Ile Thr Asp Lys Thr Val Leu Asp Met Lys Ala
1               5                   10                  15

Met Asp Ser Lys
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence:  partial
      synthetic TCR alpha chain

<400> SEQUENCE: 13

Lys Thr Met Glu Ser Gly Thr Phe Ile Thr Asp Lys Thr Val Leu Asp
1               5                   10                  15

Met Lys Ala Met
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence:  partial
      synthetic TCR alpha chain

<400> SEQUENCE: 14

Tyr Ile Gln Asn Pro Glu Pro Ala Val Tyr Gln Leu Lys Asp Pro Arg
1               5                   10                  15

Ser Gln Asp Ser
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence:  partial
      synthetic TCR alpha chain

<400> SEQUENCE: 15

Ala Val Tyr Gln Leu Lys Asp Pro Arg Ser Gln Asp Ser Thr Leu Cys
1               5                   10                  15

Leu Phe Thr Asp
            20

<210> SEQ ID NO 16
<211> LENGTH: 20
```

```
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 16

Asn Gly Arg Glu Val His Ser Gly Val Ser Thr Asp Pro Gln Ala Tyr
1               5                   10                  15

Lys Glu Ser Asn
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 17

Lys Glu Ser Asn Tyr Ser Tyr Cys Leu Ser Ser Arg Leu Arg Val Ser
1               5                   10                  15

Ala Thr Phe Trp
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 18

Pro Pro Lys Val Ser Leu Phe Glu Pro Ser Lys Ala Glu Ile Ala Asn
1               5                   10                  15

Lys Gln Lys Ala
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 19

Arg Glu Val His Ser Gly Val Ser Thr Asp Pro Gln Ala Tyr Lys Glu
1               5                   10                  15

Ser Asn Tyr Ser
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: partial
      synthetic TCR beta chain

<400> SEQUENCE: 20

Val Thr Pro Pro Lys Val Ser Leu Phe Glu Pro Ser Lys Ala Glu Ile
1               5                   10                  15
```

Ala Asn Lys Gln
        20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 21
cacagacaaa tgtgtgctag acat                                         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 22
atgtctagca cacatttgtc tgtg                                         24

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 23
cagtggggtc tgcacagacc c                                            21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 24
gggtctgtgc agaccccact g                                            21

<210> SEQ ID NO 25
<211> LENGTH: 627
<212> TYPE: DNA
<213> ORGANISM: Artificial Sequence
<220> FEATURE:
<223> OTHER INFORMATION: Description of Artificial Sequence: coding
      sequence for soluble CD1-binding TCR alpha chain

<400> SEQUENCE: 25
atgaaccaag tggagcagag tcctcagtcc ctgatcatcc tggagggaaa gaactgcact    60
cttcaatgca attatacagt gagccccttc agcaacttaa ggtggtataa gcaagatact   120
gggagaggtc ctgtttccct gacaatcatg actttcagtg agaacacaaa gtcgaacgga   180
agatatacag caactctgga tgcagacaca aagcaaagct ctctgcacat cacagcctcc   240
cagctcagcg attcagcctc ctacatctgt gtggtgagcg acagaggctc aaccctgggg   300
aggctatact ttggaagagg aactcagttg actgtctggc ctgatatcca gaaccccgat   360
cctgccgtgt accagctgag agactctaaa tccagtgaca gtctgtctg cctattcacc    420 gattttgatt ctcaaacaaa tgtgtcacaa agtaaggatt ctgatgtgta tatcacagac   480
aaatgtgtgc tagacatgag gtctatggac ttcaagagca cagtgctgt ggcctggagc    540

-continued

```
aacaaatctg actttgcatg tgcaaacgcc ttcaacaaca gcattattcc agaagacacc      600
ttcttcccca gcccagaaag ttcctaa                                         627
```

<210> SEQ ID NO 26
<211> LENGTH: 732
<212> TYPE: DNA
<213> ORGANISM: Artificial Sequence
<220> FEATURE:
<223> OTHER INFORMATION: Description of Artificial Sequence: coding
      sequence for soluble CD1-binding TCR beta chain

<400> SEQUENCE: 26

```
atggacatct accagacccc aagatacctt gttataggga caggaaagaa gatcactctg      60
gaatgttctc aaaccatggg ccatgacaaa atgtactggt atcaacaaga tccaggaatg     120
gaactacacc tcatccacta ttcctatgga gttaattcca cagagaaggg agatctttcc     180
tctgagtcaa cagtctccag aataaggacg gagcattttc ccctgaccct ggagtctgcc     240
aggccctcac atacctctca gtacctctgt gccagcagtg aaaacatagg gacagcctac     300
gagcagtact cgggccgggg caccaggctc acggtcacag gggacctgaa aacgtgttc      360 ccacccgagg tcgctgtgtt tgagccatca gaagcagaga tctcccacac ccaaaaggcc     420
acactggtgt gcctggccac aggcttctac cccgaccacg tggagctgag ctggtgggtg     480
aatgggaagg aggtgcacag tggggtctgc acagaccgc agcccctcaa ggagcagccc      540 gcccctcaatg actccagata cgctctgagc agccgcctga ggtctcggc caccttctgg     600 caggaccccc gcaaccactt ccgctgtcaa gtccagttct acgggctctc ggagaatgac     660
gagtggaccc aggatagggc caaacccgtc acccagatcg tcagcgccga ggcctggggt     720
agagcagact aa                                                         732
```

<210> SEQ ID NO 27
<211> LENGTH: 208
<212> TYPE: PRT
<213> ORGANISM: Artificial Sequence
<220> FEATURE:
<223> OTHER INFORMATION: Description of Artificial Sequence: soluble
      CD1-binding TCR alpha chain

<400> SEQUENCE: 27

```
Met Asn Gln Val Glu Gln Ser Pro Gln Ser Leu Ile Ile Leu Glu Gly
 1               5                   10                  15

Lys Asn Cys Thr Leu Gln Cys Asn Tyr Thr Val Ser Pro Phe Ser Asn
             20                  25                  30

Leu Arg Trp Tyr Lys Gln Asp Thr Gly Arg Gly Pro Val Ser Leu Thr
         35                  40                  45

Ile Met Thr Phe Ser Glu Asn Thr Lys Ser Asn Gly Arg Tyr Thr Ala
     50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val Ser Asp Arg Gly
                 85                  90                  95

Ser Thr Leu Gly Arg Leu Tyr Phe Gly Arg Gly Thr Gln Leu Thr Val
            100                 105                 110

Trp Pro Asp Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140
```

```
Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
                195                 200                 205

<210> SEQ ID NO 28
<211> LENGTH: 243
<212> TYPE: PRT
<213> ORGANISM: Artificial Sequence
<220> FEATURE:
<223> OTHER INFORMATION: Description of Artificial Sequence:  soluble
      CD1-binding TCR beta chain

<400> SEQUENCE: 28

Met Asp Ile Tyr Gln Thr Pro Arg Tyr Leu Val Ile Gly Thr Gly Lys
1               5                   10                  15

Lys Ile Thr Leu Glu Cys Ser Gln Thr Met Gly His Asp Lys Met Tyr
                20                  25                  30

Trp Tyr Gln Gln Asp Pro Gly Met Glu Leu His Leu Ile His Tyr Ser
            35                  40                  45

Tyr Gly Val Asn Ser Thr Glu Lys Gly Asp Leu Ser Ser Glu Ser Thr
        50                  55                  60

Val Ser Arg Ile Arg Thr Glu His Phe Pro Leu Thr Leu Glu Ser Ala
65                  70                  75                  80

Arg Pro Ser His Thr Ser Gln Tyr Leu Cys Ala Ser Ser Glu Asn Ile
                85                  90                  95

Gly Thr Ala Tyr Glu Gln Tyr Phe Gly Pro Gly Thr Arg Leu Thr Val
                100                 105                 110

Thr Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp
```